United States Patent [19]

Skuballa et al.

[11] 4,315,013
[45] Feb. 9, 1982

[54] CERTAIN PYRROLE ANALOGS OF PROSTACYCLIN DERIVATIVES

[75] Inventors: Werner Skuballa; Bernd Raduechel; Helmut Vorbrueggen; Gerda Mannesmann; Wolfgang Losert; Jorge Casals, all of Berlin, Fed. Rep. of Germany

[73] Assignee: Schering, Aktiengesellschaft, Berlin and Bergkamen, Fed. Rep. of Germany

[21] Appl. No.: 122,794

[22] Filed: Feb. 19, 1980

[30] Foreign Application Priority Data

Feb. 20, 1979 [DE] Fed. Rep. of Germany ....... 2907118

[51] Int. Cl.³ ................... A61K 31/40; C07D 209/52; C07D 401/12; C07D 405/12; A61K 31/435
[52] U.S. Cl. ............................... 424/263; 260/326.27; 424/274; 544/238; 544/298; 544/405; 548/187; 548/225; 546/272
[58] Field of Search ................... 260/376.27; 424/274, 424/263; 546/281

[56] References Cited

U.S. PATENT DOCUMENTS

| | | | |
|---|---|---|---|
| 4,097,489 | 6/1978 | Bundy | 260/326.27 |
| 4,151,176 | 4/1979 | Bundy | 260/326.27 |
| 4,161,584 | 7/1979 | Bundy | 260/326.27 |
| 4,211,706 | 7/1980 | Bundy | 260/326.27 |

FOREIGN PATENT DOCUMENTS 2826096  1/1979 Fed. Rep. of Germany ........................ 260/326.27

OTHER PUBLICATIONS

Bundy et al., Tet. Letters, No. 16, pp. 1371-1374, (1978).

*Primary Examiner*—Alton D. Rollins
*Attorney, Agent, or Firm*—Millen & White

[57] ABSTRACT

Prostane derivatives of the formula

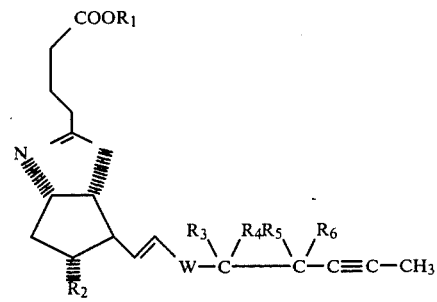

wherein
$R_1$ is (a) hydrogen, (b) $C_{1-10}$ alkyl, (c) $C_{1-10}$ alkyl substituted by halogen; $C_{1-4}$ alkoxy; $C_{6-10}$ aryl; $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$alkylammonium; (d) $C_{4-10}$ cycloalkyl, (e) $C_{4-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S;
W is hydroxymethylene or RO-methylene; or

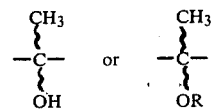

wherein OH or OR is in the α-position and
R is an in vivo hydrolyzable and physiologically acceptable ether or acyl group which is conventional for modifying OH groups in prostaglandins;
$R_3$, $R_4$, $R_5$ and $R_6$ are each independently hydrogen or alkyl of 1-5 carbon atoms,
$R_2$ is OH or OR, R being as defined above,
or, when $R_1$ is H, a physiologically compatible salt thereof with a base.

17 Claims, No Drawings

CERTAIN PYRROLE ANALOGS OF PROSTACYCLIN DERIVATIVES

BACKGROUND OF THE INVENTION

The present invention relates to novel prostacyclin derivatives, a process for their preparation and their use as medicinal agents.

Prostacyclin ($PGI_2$), one of the primary factors in blood platelet aggregation, has a dilating effect on various blood vessels (Science 196: 1072) and thus can be considered an agent for lowering blood pressure. However, $PGI_2$ does not exhibit the stability required for medicinal agents. Thus, the half-life of $PGI_2$ at physiological pH values and at room temperature is merely a few minutes.

Moreover, G. L. Bundy et al, Tetrahedron Letters 1978: 1371 and DOS (German Unexamined Laid-Open Application) No. 2,826,096, disclose 9α,6-nitriloprostaglandins.

SUMMARY OF THE INVENTION

Accordingly, it is an object of this invention to provide new prostacyclin derivatives which have valuable medicinal properties.

Upon further study of the specification and appended claims, further objects and advantages of this invention will become apparent to those skilled in the art.

These objects have been attained by this invention by providing prostane derivatives of Formula I

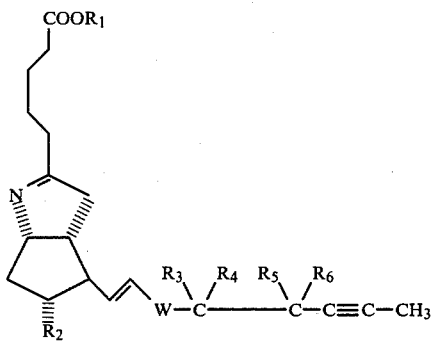

wherein
$R_1$ is hydrogen, alkyl, cycloalkyl, aryl or a heterocyclic residue,
W is free or functionally modified hydroxymethylene or a free or functionally modified

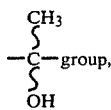

the OH-group being in the α-position, and
$R_3$, $R_4$, $R_5$ and $R_6$ are each hydrogen or alkyl of 1-5 carbon atoms, and
$R_2$ is free or functionally modified hydroxy, and
when $R_1$ is hydrogen, the physiologically compatible salts thereof with a base.

It has now been found that, by the introduction of a triple bond and, optionally, alkyl groups into the lower chain of 9-deoxy-9α,6-nitrilo-PGF, it is possible to obtain a longer duration of efficacy, a higher selectivity, and a higher effectiveness of pharmacological activity.

DETAILED DISCUSSION

Suitable alkyl groups $R_1$ include straight or branched alkyl groups of 1-10 carbon atoms, e.g., methyl, ethyl, propyl, butyl, isobutyl, tert-butyl, pentyl, neopentyl, heptyl, hexyl, decyl, etc. Preferred alkyl groups $R_1$ are those of 1-4 carbon atoms, such as, for example, methyl, ethyl, propyl, isopropyl, isobutyl, butyl, etc.

Equivalent alkyl groups $R_1$ are such $C_{1-10}$ alkyl groups mono- to polysubstituted by halogen, $C_{1-4}$ alkoxy, optionally substituted $C_{1-10}$ aryl groups such as those described below as $R_1$ groups per se, di-$C_{1-4}$-alkylamino and tri-$C_{1-4}$-alkylammonium. Monosubstituted alkyl groups are preferred. Examples of such substituents are fluorine, chlorine, bromine, phenyl, dimethylamino, diethylamino, methoxy, ethoxy, etc.

Suitable aryl groups $R_1$ include substituted as well as unsubstituted aryl groups, e.g., phenyl, 1-naphthyl, and 2-naphthyl, each of which can be substituted by 1-3 halogen atoms, phenyl, 1-3 alkyl groups each of 1-4 carbon atoms, or a chloromethyl, fluoromethyl, trifluoromethyl, carboxy, hydroxy, or $C_{1-4}$ alkoxy group. Substitution in the 3- and 4-positions on the phenyl ring is preferred, for example, by fluorine, chlorine, alkoxy or trifluoromethyl; or in the 4-position by hydroxy.

The cycloalkyl group $R_1$ can contain 4-10, preferably 5 or 6 carbon atoms in the ring. The rings can be substituted by alkyl groups of 1-4 carbon atoms. Examples include cyclopentyl, cyclohexyl, methylcyclohexyl and adamantyl.

Suitable heterocyclic groups $R_1$ include 5- and 6-membered aromatic heterocycles containing at least one hetero atom, preferably nitrogen, oxygen, or sulfur. Examples include 2-furyl, 2-thienyl, 2-pyridyl, 3-pyridyl, 4-pyridyl, oxazolyl, thiazolyl, pyrimidinyl, pyridazinyl, pyrazinyl and others.

The hydroxy groups for $R_2$ and in W can independently be functionally modified, for example, by etherification or esterification, wherein the free or modified hydroxy groups in W as hydroxymethylene can be in the α- or β-position, free hydroxy groups being preferred. Suitable ether and acyl residues are fully conventional and well-known to persons skilled in the art, e.g., are in vivo hydrolyzable and physiologically acceptable ether or acyl groups which are conventional for modifying OH groups in prostacyclin-type compounds. Preferred are readily cleavable ester residues, such as, for example, tetrahydropyranyl, tetrahydrofuranyl, α-ethoxyethyl, trimethylsilyl, dimethyl-tert-butylsilyl and tribenzylsilyl. Suitable acyl residues include those of $C_{1-15}$ hydrocarbon carboxylic or sulfonic acids. Examples of such suitable acyl residues include: acetyl, propionyl, butyryl, benzoyl, etc.

In general, these conventional protective groups include, e.g., those disclosed in Mc. Omie. Ed., Protective Groups in Organic Chemistry, Plenum Press, N.Y., 1973, whose disclosure is incorporated by reference herein.

Suitable alkyl groups for each of $R_3$, $R_4$, $R_5$ and $R_6$ independently include straight-chain and branched alkyl of 1-5 carbon atoms, e.g., methyl, ethyl, propyl, isopropyl, butyl, isobutyl, tert-butyl, pentyl, isopentyl, neopentyl, etc. Methyl and ethyl are preferred.

For salt formation with the free acids ($R_1$=H) of Formula I, any of the inorganic or organic bases which are conventionally employed by persons skilled in the art for the formation of physiologically compatible salts may be used. These are well-known. Examples include: alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine, etc.

The present invention furthermore relates to a process for preparing the prostane derivatives of Formula I, comprising conventionally thermally treating a compound of Formula II

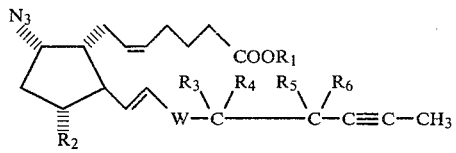

wherein $R_1$, $R_2$, $R_3$, $R_4$, $R_5$, $R_6$ and W are as defined above, in an inert solvent, and optionally, thereafter, in any desired sequence, liberating blocked hydroxy groups and/or esterifying or etherifying a free hydroxy group and/or esterifying any free carboxy group and/or saponifying any esterified carboxy groups, or converting a carboxy group into a physiologically compatible salt with a corresponding base.

The thermal reaction of the compound of Formula II may be conducted at a temperature of 20°–150° C., preferably 40°–120° C. For the preferred temperature range, suitable inert solvents include the following, for example: ethyl acetate, methyl acetate, tetrahydrofuran, dimethoxyethane, carbon tetrachloride, methylene chloride, 1,2-dichloroethane, dimethylformamide, etc. The reaction is fully conventional (DE-OS No. 28 26 096).

A resultant prostaglandin ester can be saponified by any of the conventional methods known to those skilled in the art, for example, using an alkaline catalyst. The introduction of an ester group wherein $R_1$ is an alkyl group of 1–10 carbon atoms, can also be accomplished by conventional methods known to persons skilled in the art. The carboxy compounds can be reacted, for example, with a diazo hydrocarbon in a manner known per se. The esterification with such a diazo hydrocarbon can be accomplished, for example, by mixing a solution of the diazo hydrocarbon in an inert solvent, preferably in diethyl ether, with the carboxy compound in the same or in another solvent, e.g., methylene chloride. After the reaction is completed (generally within 1–30 minutes), the solvent is removed and the ester purified in conventional fashion. Diazoalkanes are either known or can be produced according to conventional methods (Org. Reactions, 8: 389–394 (1954)).

The introduction of an ester group $R_1$ wherein $R_1$ is a substituted or unsubstituted aryl group, can also be performed using conventional methods known to those skilled in the art. For example, the carboxy compounds can be reacted in an inert solvent with the corresponding aryl hydroxy compound using dicyclohexylcarbodiimide in the presence of a suitable base, for example, pyridine or triethylamine. Suitable solvents include methylene chloride, ethylene chloride, chloroform, ethyl acetate, tetrahydrofuran, etc., and preferably chloroform. The reaction is generally conducted at a temperature of −30° C. to +50° C., preferably at about +10° C.

The prostaglandin derivatives of Formula I wherein $R_1$ is hydrogen can be converted into salts using suitable amounts of the corresponding inorganic bases under conventional neutralization conditions. For example, after dissolving the corresponding PG acid in water containing a stoichiometric amount of the base, the solid inorganic salt can be obtained after evaporation of the water or after the addition of a water-miscible solvent, e.g., alcohol or acetone.

For the production of an amine salt, which is also conventional, the PG acid is dissolved, for example, in a suitable solvent, e.g., ethanol, acetone, diethyl ether or benzene, and at least a stoichiometric amount of the amine is added to this solution. During this procedure, the salt is ordinarily obtained in the solid form or is isolated in the usual way after evaporation of the solvent.

Functional modification of the free OH-groups likewise can be achieved using methods known to those skilled in the art. To introduce ether blocking groups, the reaction can be conducted, for example, with dihydropyran in methylene chloride or chloroform using an acidic condensation agent, such as, for example, p-toluenesulfonic acid. The dihydropyran is employed in excess, preferably in two to ten times the amount of the theoretical requirement. The reaction is normally terminated Formula I with a carboxylic acid derivative, e.g., an acid chloride, an acid anhydride, and others.

The liberation of a functionally modified OH-group to generate the corresponding OH-containing compounds of Formula I again may be accomplished according to methods known per se. For example, ether blocking groups can be split off in an aqueous solution of an organic acid, e.g., acetic acid, propionic acid, etc. To improve solubility, a water-miscible, inert organic solvent is advantageously added. Suitable organic solvents include, for example, alcohols, such as methanol and ethanol, and ethers, such as dimethoxyethane, dioxane, and tetrahydrofuran. Tetrahydrofuran is preferably employed. The splitting-off step is effected preferably at temperature of 20°–80° C.

The silyl ether blocking groups are split off, for example, using tetrabutylammonium fluoride. Examples of suitable solvents include tetrahydrofuran, diethyl ether, dioxane, methylene chloride, etc. The splitting off step is preferably accomplished at temperatures of 0°–80° C.

Acyl groups can be saponified, for example, using alkali or alkaline earth metal carbonates or hydroxides in an alcohol or in an aqueous solution of an alcohol. Suitable alcohols include aliphatic alcohols, e.g., methanol, ethanol, butanol, etc., preferably methanol. Examples of alkali carbonates and hydroxides include potassium and sodium salts, the potassium salts being preferred. Suitable alkaline earth carbonates and hydroxides include, for example, calcium carbonate, calcium hydroxide and barium carbonate. The reaction takes place at −10° C. to 70° C., preferably at about 25° C.

The azide of Formula II utilized as the starting material for the above-described process can be prepared by first converting an alcohol of Formula III

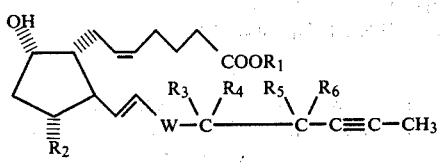

(DOS No. 2,729,960) wherein free hydroxy groups in $R_2$ and W are blocked, for example, as tetrahydropyranyl ethers, with p-toluenesulfonic acid chloride into the tosylate of Formula IV

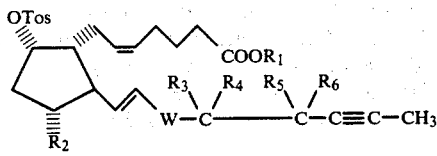

By reacting the product, e.g., with potassium nitrite in dimethyl sulfoxide, the 9β-configured alcohol V can be obtained

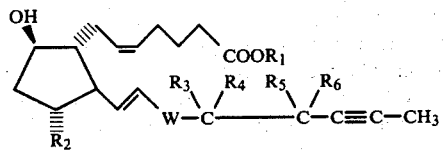

In turn, this can be reacted with p-toluenesulfonic acid chloride in the presence of pyridine to produce the tosylate of Formula VI

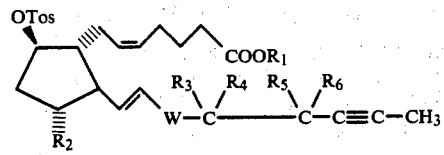

At this stage, the tetrahydropyranyl ether blocking groups can, optionally, be split off. The tosylate is subsequently converted by reaction with sodium azide in a polar, aprotic solvent, such as DMF, N-methylpyrrolidone, or preferably HMPA (hexamethylphosphoric triamide), into the azide of Formula II, which can be optionally saponified ($R_1$ equals H).

The compounds of this invention have a blood-pressure-lowering and bronchodilatory effect. They are also effective in inhibiting thrombocyte aggregation.

Consequently, the novel prostacyclin derivatives of this invention are valuable pharmaceuticals, since they display, with a similar spectrum of efficacy, an improved specificity and, above all, a substantially longer effectiveness as compared with corresponding prostaglandins. As compared with $PGI_2$, they are distinguished by a higher stability.

The high tissue specificity of the novel prostaglandins of this invention can be observed in tests on smooth muscle organs, such as, for example, on the guinea pig ileum or on the isolated rabbit trachea, where a substantially lower stimulation is seen than with the administration of natural prostaglandins of the E-, A- or F-type.

The novel prostaglandin analogs possess the properties typical for prostacyclins, such as, for example, lowering of the peripheral arterial and coronary vascular resistance and, thus, lowering of the systemic blood pressure without simultaneously lowering the cardiac output and the coronary blood suffusion; inhibition of thrombocyte aggregation; inhibition of bronchoconstriction; inhibition of gastric acid secretion; antiallergic properties; lowering of the pulmonary vascular resistance and pulmonary blood pressure; promotion of renal blood suffusion; and increasing of cerebral blood suffusion. In addition, the prostaglandins of this invention have antiproliferative properties.

Upon intravenous injection of nonanesthesized, hypertonic rats in dosages of 5, 20 and 100 μg/kg of body weight, the compounds of this invention show a stronger blood-pressure-lowering effect of a longer duration than $PGE_2$ and $PGA_2$, without triggering, as $PGE_2$, diarrheas or, as $PGA_2$, cardiac arrhythmias.

Upon intravenous injection of narcotized rabbits, the compounds of this invention, as compared to $PGE_2$ and $PGA_2$, show a stronger lowering of the blood pressure of a considerably longer duration, without affecting other smooth-muscle organs or organ functions.

The present invention, accordingly, also concerns medicinal agents based on the compounds of this invention and conventional adjuvants and excipients. For example, the active agents of this invention, e.g., in conjunction with the excipients known and customary in galenic pharmacy, can be used as blood-pressure-lowering medicines, e.g., as antihypertensives.

The pharmacologically active compounds of this invention can be processed in accordance with conventional methods of galenic pharmacy to produce medicinal agents, especially for oral administration, in human and veterinary medicine, e.g., to mammals including humans.

Conventional excipients are pharmaceutically acceptable organic or inorganic carrier substances suitable for parenteral, enteral or topical application which do not deleteriously react with the active compounds. Suitable pharmacologically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acaid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.01–100 mg in a pharmaceutically acceptable carrier per unit dosage.

The dosage of the compounds according to this invention is 1–5000 μg/kg/day when administered to patients, e.g., humans, as drugs for the treatment of the mentioned diseases, e.g., as antihypertensives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(13E)-(11R,15S)-11,15-Dihydroxy-9α,6-nitrilo-13-prosten-18-ynoic Acid

A solution of 365 mg. of (5A,13E)-(9S,11R,15S)-9-azido-11,15-dihydroxy-5,13-prostadien-18-ynoic acid in 30 ml. of ethyl acetate is stirred for 27 hours at 70°–80° under argon. The mixture is then evaporated under vacuum and the residue chromatographed on silica gel. With methylene chloride/isopropanol (1+1), 230 mg. of the title compound is obtained as a viscous oil.

IR (CHCl$_3$): 3610, 3400 (broad), 2940, 2862, 1720, 1640, 1023, 1078, 975 cm$^{-1}$.

The starting material for the above title compound is prepared as follows:

1(a)

(5Z,13E)-(9S,11R,15S)-11,15-Bis(tetrahydropyran-2-yloxy)-9-(p-toluenesulfonyloxy)-5,13-prostadien-18-ynoic Acid Methyl Ester At 0°, 1.38 g. of p-toluenesulfonyl chloride is added to a solution of 2 g. of (5Z,13E)-(9S,11R,15S)-11,15-bis(tetrahydropyran-2-yloxy)-9-hydroxy-5,13-prostadien-18-ynoic methyl ester (prepared from the corresponding acid with ethereal diazomethane solution) in 4 ml. of pyridine. The mixture is stirred for 6 hours at room temperature and then allowed to stand at 5° for 60 hours. The mixture is then diluted with ether, shaken in succession once with water, once with ice-cold 3% sulfuric acid, once with water, once with 5% sodium bicarbonate solution, twice with water, and dried over magnesium sulfate and evaporated under vacuum, thus obtaining 2.45 g. of the title compound as a colorless oil.

IR: 2960, 2880, 1732, 1605, 1493, 1370, 1178, 977 cm$^{-1}$.

1(b)

(5Z,13E)-(9R,11R,15S)-11,15-Bis(tetrahydropyran-2-yloxy)-9-hydroxy-5,13-prostadien-18-ynoic Acid Methyl Ester A solution of 2.4 g. of the tosylate prepared according to Example 1(a) in 50 ml. of dimethyl sulfoxide is combined with 5.1 g. of potassium nitrite and the mixture is stirred for 4 hours at 65°. Then the mixture is poured on a 20% sodium chloride solution, extracted five times with respectively 50 ml. of a mixture of pentane/ether (1+1), the organic phase is washed three times with respectively 50 ml. of water, dried over magnesium sulfate, and evaporated under vacuum. Chromatography of the residue on silica gel yields, with ether/pentane (8+2), 1.25 g. of the inverted alcohol as a colorless oil.

IR: 3400, 2950, 1730, 1440, 975 cm$^{-1}$.

1(c)

(5Z,13E)-(9R,11R,15S)-11,15-Bis(tetrahydropyran-2-yloxy)-9-(p-toluenesulfonyloxy)-5,13-prostadien-18-ynoic Acid Methyl Ester At 0°, 622 mg. of p-toluenesulfonyl chloride is added to a solution of 0.9 g. of the 9β-alcohol prepared according to Example 1(b) in 5 ml. of pyridine. The mixture is stirred for 21 hours at room temperature under argon. The reaction mixture is then diluted with ether and shaken in succession with water, ice-cold 3% sulfuric acid, water, 5% sodium bicarbonate solution, three times with water. The mixture is dried over magnesium sulfate and evaporated under vacuum, thus obtaining 1.09 g. of the tosylate as a colorless oil.

IR: 2962, 1732, 1605, 1493, 1370, 975 cm$^{-1}$.

1(d)

(5Z,13E)-(9R,11R,15S)-11,15-Dihydroxy-9-(p-toluenesulfonyloxy)-5,13-prostadien-18-ynoic Acid Methyl Ester 1.06 g. of the tosylate produced according to Example 1(c) is stirred for 20 hours with 30 ml. of a mixture of acetic acid/water/tetrahydrofuran (65+35+10) under argon. The mixture is evaporated under vacuum and the residue purified by preparative layer chromatography. With ether as the eluent, 485 mg. of the title compound is obtained as a colorless oil.

IR: 3610, 3430, 2963, 2940, 1730, 1603, 1363, 1178, 975 cm$^{-1}$.

1(e)

(5Z,13E)-(9S,11R,15S)-9-Azido-11,15-dihydroxy-5,13-prostadien-18-ynoic Acid Methyl Ester A solution of 80 mg. of the diol prepared according to Example 1(d) in 1.6 ml. of hexamethylphosphoric triamide is combined with 10.8 g. of sodium azide and agitated for 6 hours at 40°. The mixture is combined with 6 ml. of a 20% sodium chloride solution, extracted five times with a mixture of ether/pentane (3+1), the organic phase is shaken twice with respectively 3 ml. of water, dried with magnesium sulfate, and evaporated under vacuum. The title compound is thus obtained as an oil which is uniform as determined by thin-layer chromatography.

IR: 3400, 2960, 2110, 1730, 975 cm$^{-1}$.

1(f)

(5Z,13E)-(9S,11R,15S)-9-Azido-11,15-dihydroxy-5,13-prostadien-18-ynoic Acid 70 mg. of the azide prepared according to Example 1(e) is combined with 2 ml. of a solution of 50 mg. of potassium hydroxide in 1.65 ml. of methanol and 0.35 ml. of water, and the mixture is stirred for 4 hours at room temperature under argon. The mixture is then cooled to 5°, acidified with 10% citric acid solution to pH 6, extracted three times with methylene chloride, the organic extract is washed twice with respectively 5 ml. of brine, dried over magnesium sulfate, and evaporated under vacuum. After chromatography of the residue on silica gel, 39 mg. of the title compound is obtained with ethyl acetate in the form of a colorless oil.

IR: 3600, 3400 (broad), 2110, 1715, 1605, 976 cm$^{-1}$.

EXAMPLE 2

(13E)-(11R,15S,16RS)-11,15-Dihydroxy-16-methyl-9α,6-nitrilo-13-prosten-18-ynoic Acid A solution of 520 mg. of (5Z,13E)-(9S,11R,15S,16RS)-9-azido-11,15-dihydroxy-16-methyl-5,13-prostadien-18-ynoic acid in 50 ml. of ethyl acetate is agitated for 26 hours at 70°–80° under argon. The mixture is subsequently evaporated under vacuum and the residue chromatographed on silica gel. With methylene chloride/isopropanol (1+1), 380 mg. of the title compound is obtained as a colorless oil.

IR: 3600, 3400 (broad), 2942, 2860, 1720, 1640, 1080, 1025, 976 cm$^{-1}$.

The starting material for the above title compound is produced as follows:

2(a)
(5Z,13E)-(9S,11R,15S,16RS)-11,15-Bis(tetrahydropyran-2-yloxy)-16-methyl-9-(p-toluenesulfonyloxy)-5,13-prostadien-18-ynoic Acid Methyl Ester At 0°, 2.15 g. of p-toluenesulfonyl chloride is addded to a solution of 3.05 g. of (5Z,13E)-(9S,11R,15S,16RS)-11,15-bis(tetrahydropyran-2-yloxy)-9-hydroxy-16-methyl-5,13-prostadien-18-ynoic acid methyl ester (prepared from the corresponding acid with ethereal diazomethane solution) in 6 ml. of pyridine, agitated for 6 hours at room temperature and then allowed to stand for 60 hours at 5°. The mixture is then diluted with ether, shaken in succession once with water, once with ice-cold 3% sulfuric acid, once with water, once with 5% sodium bicarbonate solution, twice with water, and dried over magnesium sulfate and evaporated under vacuum, thus obtaining 3.7 g. of the tosylate as a colorless oil.

IR: 2960, 2878, 1733, 1605, 1492, 1370, 1178, 975 cm$^{-1}$.

2(b)
(5Z,13E)-(9R,11R,15S,16RS)-11,15-Bis(tetrahydropyran-2-yloxy)-9-hydroxy-16-methyl-5,13-prostadien-18-ynoic Acid Methyl Ester A solution of 3.6 g. of the tosylate prepared according to Example 2(a) in 70 ml. of dimethyl sulfoxide is combined with 6.8 g. of potassium nitrite, and the mixture is stirred for 4 hours at 65° under argon. Thereafter the mixture is poured on a 20% sodium chloride solution, extracted five times with respectively 70 ml. of a mixture of pentane/ether (1+1), the organic phase is washed three times with respectively 60 ml. of water, dried over magnesium sulfate, and evaporated under vacuum. After chromatography of the residue on silica gel, 2.5 g. of the inverted alcohol is obtained with ether/pentane (8+2) as a colorless oil.

IR: 3410, 2950, 1732, 1440, 976 cm$^{-1}$.

2(c)
(5Z,13E)-(9R,11R,15S,16RS)-11,15-Bis(tetrahydropyran-2-yloxy)-16-methyl-9-(p-toluenesulfonyloxy)-5,13-prostadien-18-ynoic Acid Methyl Ester A solution of 2.5 g. of the 9β-alcohol prepared according to Example 2(b) in 15 ml. of pyridine is combined at 0° with 1.7 g. of p-toluenesulfonyl chloride and allowed to stand for 24 hours at room temperature. The mixture is combined with 0.5 ml. of water and allowed to stand for another hour at room temperature. Thereafter the mixture is diluted with ether, shaken in succession with ice-cold 3% sulfuric acid, sodium bicarbonate solution, and water, dried over magnesium sulfate, and evaporated under vacuum, thus obtaining 3 g. of the 9β-tosylate as an oil.

IR: 2955, 1735, 1605, 1492, 1370, 975 cm$^{-1}$.

2(d)
(5Z,13E)-(9R,11R,15S,16RS)-11,15-Dihydroxy-16-methyl-9-(p-toluenesulfonyloxy)-5,13-prostadien-18-ynoic Acid Methyl Ester 2.90 g. of the 9β-tosylate prepared according to Example 2(c) is stirred for 24 hours with 80 ml. of a mixture of acetic acid/water/tetrahydrofuran (65/35/10), evaporated under vacuum, and the residue is purified by chromatography over silica gel with hexane/ethyl acetate mixtures, thus obtaining 1.40 g. of the 11,15-diol as a colorless oil.

IR: 3600, 3400, 2958, 1735, 1605, 1368, 978 cm$^{-1}$.

2(e)
(5Z,13E)-(9S,11R,15S,16RS)-9-Azido-11,15-dihydroxy-16-methyl-5,13-prostadien-18-ynoic Acid Methyl Ester One gram of the diol prepared according to Example 2(d) in 20 ml. of hexamethylphosphoric triamide and 130 mg. of sodium azide are stirred for 6 hours at 40°. The mixture is cooled, combined with 100 ml. of sodium chloride solution, and extracted several times with ether/pentane (3+1). The organic phase is washed with water, dried over magnesium sulfate, and evaporated under vacuum, thus obtaining the 9-azido compound as a viscous oil.

IR: 3600, 3420, 2958, 2110, 1735, 978 cm$^{-1}$.

2(f)
(5Z,13E)-(9S,11R,15S,16RS)-9-Azido-11,15-dihydroxy-16-methyl-5,13-prostadien-18-ynoic Acid 200 mg. of the azide prepared according to Example 2(e) is treated with methanolic potassium hydroxide solution as in Example 1(f). The crude product is chromatographed over silica gel with ethyl acetate, thus obtaining 150 mg. of the acid as a colorless oil.

IR: 3600, 3410, 2952, 2110, 1710, 978 cm$^{-1}$.

EXAMPLE 3

(13E)-(11R,15R)-11,15-Dihydroxy-16,16-dimethyl-9α,6-nitrilo-13-prosten-18-ynoic Acid A solution of 300 mg. of (5Z,13E)-(9S,11R,15R)-9-azido-11,15-dihydroxy-16,16-dimethyl-5,13-prostadien-18-ynoic acid in 25 ml. of ethyl acetate is heated for 24 hours to 70°–75° under argon. After evaporation of the solvent under vacuum, the residue is chromatographed on silica gel. With methylene chloride/10–30% isopropanol, 200 mg. of the title compound is obtained as an oil.

IR: 3600, 3400 (broad), 2950, 2860, 1715, 1640, 1020, 978 cm$^{-1}$.

The starting material for the above title compound is prepared as follows:

3(a)
(5Z,13E)-(9S,11R,15R)-11,15-Bis(tetrahydropyran-2-yloxy)-16,16-dimethyl-9-(p-toluenesulfonyloxy)-5,13-prostadien-18-ynoic Acid Methyl Ester At 0°, 3 g. of (3Z,13E)-(9S,11R,15R)-11,15-bis-(tetrahydropyran-2-yloxy)-16,16-dimethyl-9-hydroxy-5,13-prostadien-18-ynoic acid methyl ester (prepared from the carboxylic acid with ethereal diazomethane solution), dissolved in 10 ml. of pyridine, is combined with 2.09 g. of p-toluenesulfonyl chloride, and the mixture is then stirred for 48 hours at +5°. The mixture is then combined with 0.5 ml. of water, agitated for another hour, diluted with 200 ml. of ether, and washed in succession with ice-cold 10% sulfuric acid, sodium bicarbonate solution, and water, dried over magnesium sulfate, and evaporated under vacuum, thus obtaining 4 g. of the 9α-tosylate, which is further used without any purification.

IR: 2960, 2868, 1735, 1602, 1360, 1175, 975 cm$^{-1}$.

3(b)
(5Z,13E)-(9R,11R,15R)-11,15-Bis(tetrahydropyran-2-yloxy)-16,16-dimethyl-9-hydroxyl-5,13-prostadien-18-ynoic Acid Methyl Ester 3.8 g. of the tosylate obtained according to Example 3(a) and 7.6 g. of potassium nitrite are stirred with 80 ml. of dimethyl sulfoxide for 4 hours at 65°. The mixture is then diluted with brine, extracted repeatedly with ether/pentane mixture (1+1), the organic phase is washed with brine, dried over magnesium sulfate, and evaporated under vacuum. Chromatography of the product over silica gel with hexane/ethyl acetate gradients yields 1.65 g. of the 9β-alcohol as a colorless oil.

IR: 3540, 2950, 2860, 1735, 980 cm$^{-1}$.

3(c)
(5Z,13E)-(9R,11R,15R)-11,15-Bis(tetrahydropyran-2-yloxy)-16,16-dimethyl-9-(p-toluenesulfonyloxy)-5,13-prostadien-18-ynoic Acid Methyl Ester A solution of 1.50 g. of the 9β-alcohol obtained according to Example 3(b) in 10 ml. of pyridine is combined at 0° with 1.045 g. of p-toluenesulfonyl chloride, agitated for 20 hours at room temperature, combined with 0.2 ml. of water, and worked up as described in Example 3(a), thus obtaining 2.1 g. of the 9β-tosylate as an oil.

IR: 2960, 2860, 1735, 1601, 1365, 1175, 980 cm$^{-1}$.

3(d)
(5Z,13E)-(9R,11R,15R)-11,15-Dihydroxy-16,16-dimethyl-9-(p-toluenesulfonyloxy)-5,13-prostadien-18-ynoic Acid Methyl Ester 2 g. of the 9β-tosylate obtained according to Example 3(c) is treated with acetic acid analogously to Example 1(d) to split off the tetrahydropyranyl ether blocking groups.

After purification over silica gel with hexane/ethyl acetate gradients, 1.1 g. of the 11,15-diol is obtained as an oil.

IR: 3600, 3420, 2955, 1735, 1601, 1360, 1175, 978 cm$^{-1}$.

3(e)
(5Z,13E)-(9S,11R,15R)-9-Azido-11,15-dihydroxy-16,16-dimethyl-5,13-prostadien-18-ynoic Acid Methyl Ester A solution of 1.1 g. of the compound prepared according to Example 3(d) in 20 ml. of hexamethylphosphoric triamide is heated with 150 mg. of sodium azide for 6 hours to 40°. The mixture is diluted with 150 ml. of brine, extracted repeatedly with ether/pentane mixture (3+1), the organic phase is washed with water, dried over magnesium sulfate, and then evaporated under vacuum. The crude product is purified over silica gel with hexane/ethyl acetate mixtures, thus obtaining 700 mg. of the 9α-azide as an oil.

IR: 3520, 2960, 2110, 1735, 978 cm$^{-1}$.

3(f)
(5Z,13E)-(9S,11R,15R)-9-Azido-11,15-dihydroxy-16,16-dimethyl-5,13-prostadien-18-ynoic Acid 500 mg. of the compound obtained according to Example 3(e) is saponified analogously to Example 1(f), thus obtaining 400 mg. of the above-identified carboxylic acid as a colorless oil.

IR: 3600, 3400 (broad), 2955, 2110, 1712, 978 cm$^{-1}$.

EXAMPLE 4
(13E)-(11R,15RS)-11,15-Dihydroxy-15-methyl-9α,6-nitrilo-13-prosten-18-ynoic Acid 200 mg. of (5Z,13E)-(9S,11R,15RS)-9-azido-11,15-dihydroxy-15-methyl-5,13-prostadien-18-ynoic acid is heated in 20 ml. of ethyl acetate for 24 hours to 70°. After evaporation of the solvent, the mixture is chromatographed on silica gel with methylene chloride/1-0–30% isopropanol, thus obtaining 120 mg. of the title compound as an oil.

IR: 3600, 3400, 2950, 2845, 1712, 1640, 978 cm$^{-1}$.

The starting material for the above title compound is prepared as follows:

4(a)
(5Z,13E)-(9S,11R,15RS)-11,15-Bis(tetrahydropyran-2-yloxy)-15-methyl-9-(p-toluenesulfonyloxy)-5,13-prostadien-18-ynoic Acid Methyl Ester Analogously to Example 1(a), 2 g. of (5Z,13E)-(9S,11R,15RS)-11,15-bis(tetrahydropyran-2-yloxy)-9-hydroxy-15-methyl-5,13-prostadien-18-ynoic acid methyl ester (prepared from the carboxylic acid with diazomethane) is converted into 2.3 g. of oily 9α-tosylate.

IR: 2960, 2865, 1735, 1601, 1365, 1175, 975 cm$^{-1}$.

4(b)
(5Z,13E)-(9R,11R,15RS)-11,15-Bis(tetrahydropyran-2-yloxy)-9-hydroxy-15-methyl-5,13-prostadien-18-ynoic Acid Methyl Ester 2.2 g. of the tosylate prepared according to Example 4(a) is reacted analogously to Example 1(b) with potassium nitrite, thus obtaining 1.3 g. of the 9β-alcohol as a colorless oil.

IR: 3450, 2955, 1735, 978 cm$^{-1}$.

4(c)
(5Z,13E)-(9R,11R,15RS)-11,15-Bis(tetrahydropyran-2-yloxy)-15-methyl-9-(p-toluenesulfonyloxy)-5,13-prostadien-18-ynoic Acid Methyl Ester Analogously to Example 1(c), 1.3 g. of the 9β-alcohol prepared according to Example 4(b) yields 1.7 g. of the 9β-tosylate as an oil.

IR: 2960, 2860, 1735, 1601, 1370, 1175, 978 cm$^{-1}$.

4(d)
(5Z,13E)-(9R,11R,15RS)-11,15-Dihydroxy-15-methyl-9-(p-toluenesulfonyloxy)-5,13-prostadien-18-ynoic Acid Methyl Ester Analogously to Example 1(d), 1.7 g. of the compound prepared according to Example 4(c) yields 1 g. of the 11,15-diol as a colorless oil.

IR: 3600, 3450, 2960, 1735, 1601, 1365, 1178, 975 cm$^{-1}$.

4(e)
(5Z,13E)-(9S,11R,15RS)-9-Azido-11,15-dihydroxy-15-methyl-5,13-prostadien-18-ynoic Acid Methyl Ester One gram of the compound produced according to Example 4(d) is reacted analogously to Example 1(c) with sodium azide, thus obtaining 600 mg. of the 9-azido compound as a colorless oil.

IR: 3600, 2955, 2110, 1735, 975 cm$^{-1}$.

4(f)
(5Z,13E)-(9S,11R,15RS)-9-Azido-11,15-dihydroxy-15-methyl-5,13-prostadien-18-ynoic Acid 600 mg. of the compound prepared according to Example 4(e) is saponified analogously to Example 1(f), thus producing 500 mg. of the carboxylic acid as an oil.

IR: 3600, 3420 (broad), 2960, 2110, 1710, 975 cm$^{-1}$.

EXAMPLE 5
(13E)-(11R,15S)-11,15-Dihydroxy-9α,6-nitrilo-13-prosten-18-ynoic Acid Methyl Ester A solution of 150 mg. of (13E)-(11R,15S)-11,15-dihydroxy-9α,6-nitrilo-13-prosten-18-ynoic acid (see Example 1) in 10 ml. of methylene chloride is combined at −10° dropwise with an ethereal diazomethane solution until the mixture assumes a permanent yellow coloring. The mixture is evaporated under vacuum and the residue is purified by preparative thin-layer chromatography on silica gel plates with ethyl acetate/methanol (9+1) as the eluent. Yield: 120 mg. of the title compound as a colorless oil.

IR: 3450, 2960, 1735, 1642, 978 cm$^{-1}$.

EXAMPLE 6
(13E)-(11R,15S,16RS)-11,15-Dihydroxy-16-methyl-9α,6-nitrilo-13-prosten-18-ynoic Acid Methyl Ester In analogy to Example 5, (13E)-(11R,15S,16RS)-11,15-dihydroxy-16-methyl-9α,6-nitrilo-13-prosten-18-ynoic acid (see Example 2) yields the title compound as an oil.

IR: 3450, 2955, 1735, 1640, 978 cm$^{-1}$.

EXAMPLE 7
(13E)-(11R,15R)-11,15-Dihydroxy-16,16-dimethyl-9α,6-nitrilo-13-prosten-18-ynoic Acid Methyl Ester Analogously to Example 5, (13E)-(11R,15R)-11,15-dihydroxy-16,16-dimethyl-9α,6-nitrilo-13-prosten-18-ynoic acid (see Example 3) yields the title compound in the form of an oil.

IR: 3420, 2955, 1735, 1640, 975 cm$^{-1}$.

EXAMPLE 8
(13E)-(11R,15RS)-11,15-Dihydroxy-15-methyl-9α,6-nitrilo-13-prosten-18-ynoic Acid Methyl Ester Analogously to Example 5, (13E)-(11R,15RS)-11,15-dihydroxy-15-methyl-9α,6-nitrilo-13-prosten-18-ynoic acid (see Example 4) yields the title compound as an oil.

IR: 3450, 2955, 1735, 1640, 978 cm$^{-1}$.

EXAMPLE 9
Tris(hydroxymethyl)aminomethane Salt of (13E)-(11R,15S,16RS)-11,15-Dihydroxy-16-methyl-9α,6-nitrilo-13-prosten-18-ynoic Acid A solution of 181 mg. of (13E)-(11R,15S,16RS)-11,15-dihydroxy-16-methyl-9α,6-nitrilo-13-prosten-18-ynoic acid (see Example 2) in 30 ml. of acetonitrile is combined at 65° with a solution of 62 mg. of tris(hydroxymethyl)aminomethane in 0.2 ml. of water. The mixture is allowed to cool under agitation, decanted after 16 hours, and the residue is dried at 25°/0.1 torr [mm. Hg]. Yield: 160 mg. of the title compound as a waxy mass.

EXAMPLE 10
(13E)-(11R,15S,16RS)-11,15-Dihydroxy-16-methyl-9α,6-nitrilo-13-prosten-18-ynoic Acid Butyl Ester Analogously to Example 5, the acid prepared according to Example 2 yields, with diazobutane, the title compound in the form of an oil.

IR: 3430 (broad), 2960, 1737, 1640, 977 cm$^{-1}$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostane derivative of the formula

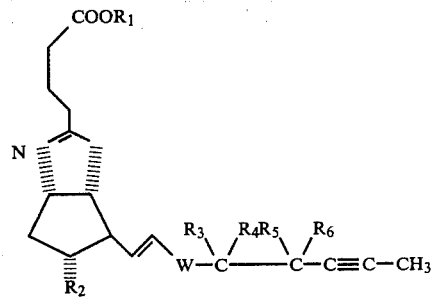

wherein
R$_1$ is (a) hydrogen, (b) C$_{1-10}$ alkyl, (c) C$_{1-10}$ alkyl substituted by halogen; C$_{1-4}$ alkoxy; C$_{6-10}$ aryl; C$_{6-10}$ aryl substituted by 1–3 halogen atoms, a phenyl group, 1–3 C$_{1-4}$ alkyl groups or a chloromethyl, fluoromethyl, trifluoromethyl, carboxy, hydroxy or C$_{1-4}$ alkoxy group; di-C$_{1-4}$-alkylamino; or tri-C$_{1-4}$-alkylammonium; (d) C$_{4-10}$ cycloalkyl, (e) C$_{4-10}$ cycloalkyl substituted by C$_{1-4}$ alkyl, (f) C$_{6-10}$ aryl, (g) C$_{6-10}$ aryl substituted by 1–3 halogen atoms, a phenyl group, 1–3 C$_{1-4}$ alkyl groups or a chloromethyl, fluoromethyl, trifluoromethyl, carboxy, hydroxy or C$_{1-4}$ alkoxy group, or (h) 2-furyl, 2-thienyl, 2-pyridyl, 3-pyridyl, or 4-pyridyl;

W is hydroxymethylene or RO-methylene; or

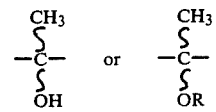

wherein OH or OR is in the α-position and

R is an in vivo hydrolyzable and physiologically acceptable ether or acyl group which is conventional for modifying OH groups in prostaglandins;

R$_3$, R$_4$, R$_5$ and R$_6$ are each indpendently hydrogen or alkyl of 1–5 carbon atoms, $R_2$ is OH or OR, R being as defined above, or, when $R_1$ is H, a physiologically compatible salt thereof with a base.

2. (13E)-(11R,15S)-11,15-Dihydroxy-9α,6-nitrilo-13-prosten-18-ynoic acid, a compound of claim 1.

3. (13E)-(11R,15S,16RS)-11,15-Dihydroxy-16-methyl-9α,6-nitrilo-13-prosten-18-ynoic acid, a compound of claim 1.

4. (13E)-(11R,15R)-11,15-Dihydroxy-16,16-dimethyl-9α,6-nitrilo-13-prosten-18-ynoic acid, a compound of claim 1.

5. (13E)-(11R,15RS)-11,15-Dihydroxy-15-methyl-9α,6-nitrilo-13-prosten-18-ynoic acid, a compound of claim 1.

6. (13E)-(11R,15S)-11,15-Dihydroxy-9α,6-nitrilo-13-prosten-18-ynoic acid methyl ester, a compound of claim 1.

7. (13E)-(11R,15S,16RS)-11,15-Dihydroxy-16-methyl-9α,6-nitrilo-13-prosten-18-ynoic acid methyl ester, a compound of claim 1.

8. (13E)-(11R,15R)-11,15-Dihydroxy-16,16-dimethyl-9α,6-nitrilo-13-prosten-18-ynoic acid methyl ester, a compound of claim 1.

9. (13E)-(11R,15RS)-11,15-Dihydroxy-15-methyl-9α,6-nitrilo-13-prosten-18-ynoic acid methyl ester, a compound of claim 1.

10. Tris(hydroxymethyl)aminomethane salt of (13E)-(11R,15S,16RS)-11,15-dihydroxy-16-methyl-9α,6-nitrilo-13-prosten-18-ynoic acid, a compound of claim 1.

11. (13E)-(11R,15S,16RS)-11,15-Dihydroxy-16-methyl-9α,6-nitrilo-13-prosten-18-ynoic acid butyl ester, a compound of claim 1.

12. A compound of claim 1, wherein:
W is hydroxymethylene or

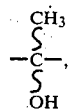

$R_2$ is OH, $R_3$ is methyl and $R_1$ is H or methyl.

13. A compound of claim 12, wherein W is hydroxymethylene.

14. A compound of claim 12 or 13, wherein $R_4$ is also methyl.

15. A prostane derivative of claim 1 wherein
R is tetrahydropyranyl, tetrahydrofuranyl, α-ethoxyethyl, trimethylsilyl, dimethyl-tert-butylsilyl, tribenzylsilyl or the acyl group of a $C_{1-15}$ hydrocarbon carboxylic or sulfonic acid.

16. A pharmaceutical composition comprising an amount of a compound of claim 1 effective for lowering blood pressure and a pharmaceutically acceptable adjuvant.

17. A method of lowering blood pressure in a host which comprises administering to the host an amount of a compound of claim 1 effective for lowering blood pressure.

* * * * *